United States Patent [19]
Overholt et al.

[11] Patent Number: 6,146,409
[45] Date of Patent: *Nov. 14, 2000

[54] THERAPEUTIC METHODS AND DEVICES FOR IRRADIATING COLUMNAR ENVIRONMENTS

[75] Inventors: Bergein F. Overholt, P.O. Box 59002, Knoxville, Tenn. 37950-9002; Masoud Panjehpour, Knoxville, Tenn.; Mike Stonefield, Vancouver, Canada

[73] Assignees: Bergein F. Overholt; Thompson Cancer Survival Center, both of Knoxville, Tenn.; QLT PhotoTherapeuticcs Inc., Canada

[*] Notice: This patent issued on a continued prosecution application filed under 37 CFR 1.53(d), and is subject to the twenty year patent term provisions of 35 U.S.C. 154(a)(2).

[21] Appl. No.: 08/716,788

[22] Filed: Sep. 4, 1996

Related U.S. Application Data

[63] Continuation of application No. 08/650,403, May 20, 1996, abandoned.

[51] Int. Cl.[7] .................................................. A61B 17/36
[52] U.S. Cl. ............................................... 607/88; 606/15
[58] Field of Search ................... 604/19–21; 606/13–16; 607/88, 89, 92

[56] References Cited

U.S. PATENT DOCUMENTS

| | | |
|---|---|---|
| 4,998,930 | 3/1991 | Lundahl . |
| 5,125,925 | 6/1992 | Lundahl . |
| 5,344,419 | 9/1994 | Spears . |
| 5,354,293 | 10/1994 | Beyer et al. . |
| 5,445,608 | 8/1995 | Chen et al. ................................. 607/89 |
| 5,454,807 | 10/1995 | Lennox et al. ............................. 606/14 |
| 5,527,308 | 6/1996 | Anderson et al. ......................... 606/14 |

FOREIGN PATENT DOCUMENTS

WO 90/00420  of 0000  WIPO .
WO 90/00914  of 0000  WIPO .

OTHER PUBLICATIONS

Allardice et al., *Gastrointestinal Endoscopy*, (1989) 35:548–551.
Beyer, W. et al., *SPIE, Optical Fibers in Medicine*, (1990) 1201:298–303.
Jocham, D. et al., *Eur. Urol.*, (1986), 2nd Suppl., 12:43–46.
Marcus, S., "Photodynamic Therapy of Human Cancer: Clinical Status, Potential, amd Needs" in Gomer, C.J. (ed.); "Future Directions and Applications in Photodynamic Therapy".
Marynissen, J.P.A., et al., *The Journal of Urology*, (1989) 142:1351–1355.
Nseyo et al., *Urology*, (1990) 36:398–402.
Overholt et al., *Lasers and Surgery in Medicine*, (1994) 14:27–33.
Overholt et al., *Gastrointestinal Endoscopy*, (1995) 42:64–70.
Overholt et al., *Seminars in Surgical Onc.*, (1995) 11:1–5.
Overholt et al., *Gastrointestinal Endoscopy*, (1993) 39(6):782–787.
Overholt et al., *Seminars in Surgical Onc.*, (1992) 8:191–203.
Panjepour et al., *Lasers and Surgery in Medicine*, (1992) 12:631–638.

*Primary Examiner*—Linda C. M. Dvorak
*Assistant Examiner*—David M. Ruddy
*Attorney, Agent, or Firm*—Morrison & Foerster

[57] ABSTRACT

The present invention provides improved methods and devices for delivering light to the surface of a biological column, for example in the treatment of Barrett's esophagus using PDT. The improvement comprises the use of an extended irradiation segment or window. The improved methods of the present invention permits treatment lengths of the biological column to be increased without increasing the incidence of stricture formation.

12 Claims, 1 Drawing Sheet

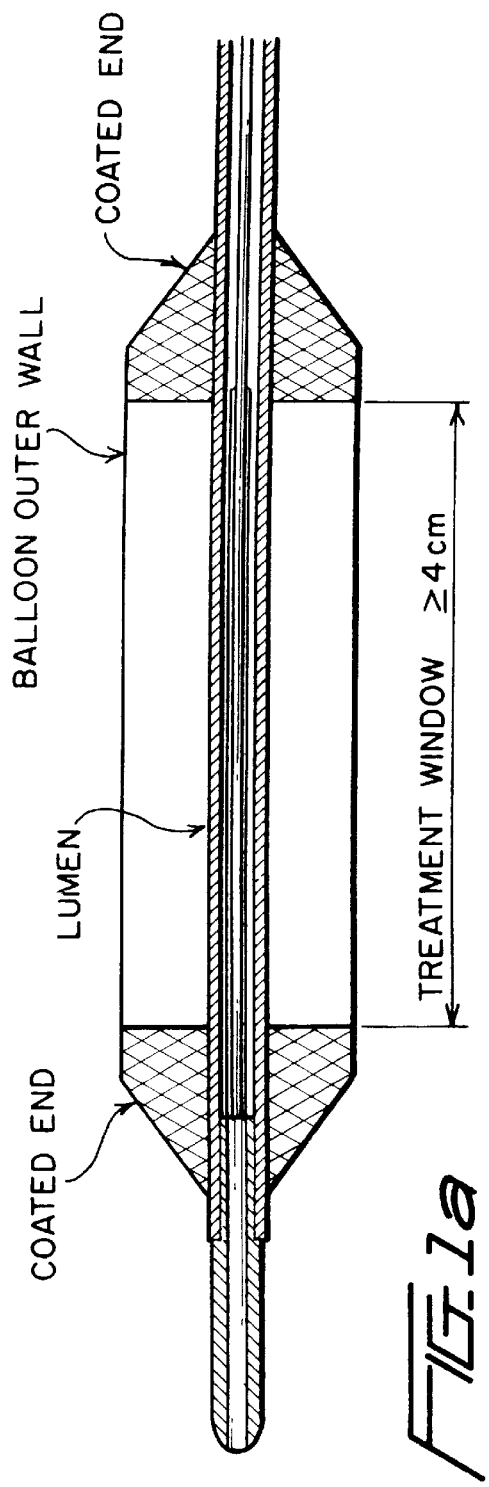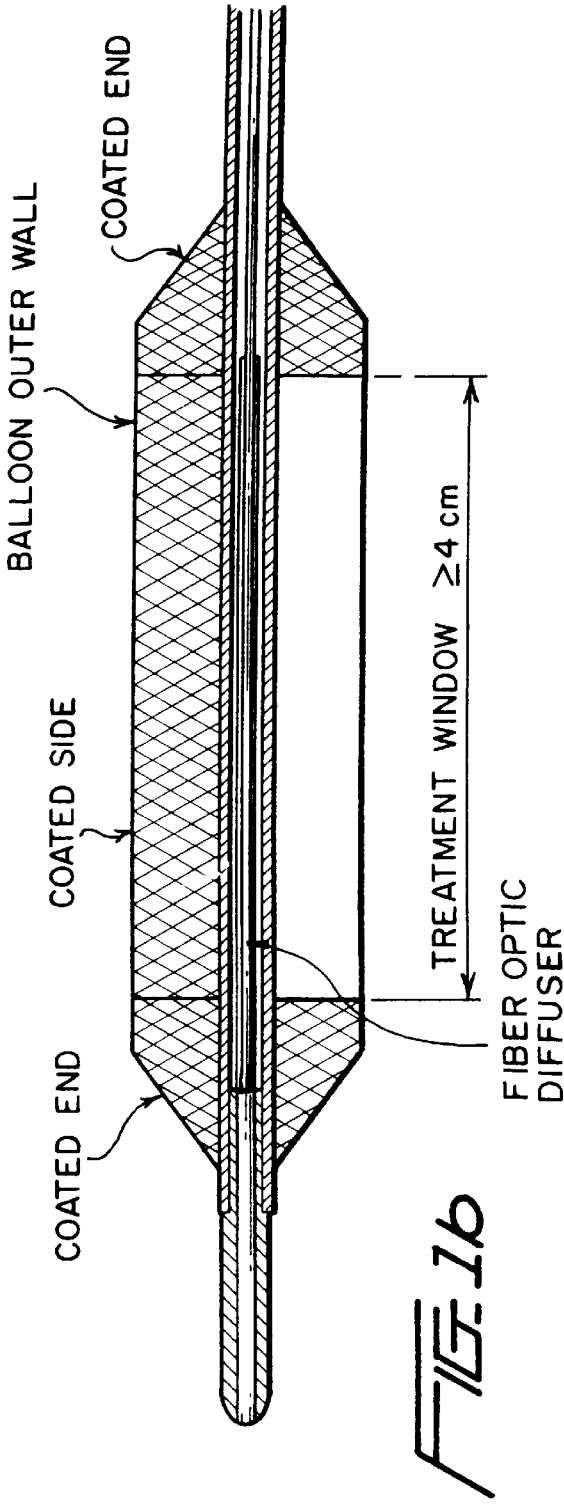

THERAPEUTIC METHODS AND DEVICES FOR IRRADIATING COLUMNAR ENVIRONMENTS

This application is a continuation of application Ser. No. 08/650,403 filed on May 20, 1996, now abandoned.

TECHNICAL FIELD

The present invention is in the field of therapeutic methods that require the administration of light to columnar environments that are located within the body of a patient, such as in photodynamic therapy (PDT) of the esophagus. The present invention provides improved methods for providing light to a biological column that involve irradiating an extended irradiation segment, such as by using a balloon catheter with extended irradiation window, to reduce the formations of strictures.

BACKGROUND ART

There are a variety of medical procedures that require light or irradiated energy to be administered to a columnar environment within the body of a patient, such as the esophagus. One example is therapeutic methods that use a light activated compound to selectively killing target cells in a patient, termed photoactivated chemotherapy. Other examples include optical diagnostic methods, hypothermia treatment and biostimulation.

In photoactivated chemotherapeutic methods, a light-sensitive drug is injected into a patient and a targeted light source is used to selectively activate the light-sensitive drug. When activated by light of a proper wavelength, the light-sensitive drug produces a cytotoxic agent that mediates the destruction of the surrounding cells or tissue.

The main application of photoactivated therapy, such as PDT, is for the destruction of malignant cell masses and precancerous cells. Photoactivated therapy has been used effectively in the treatment of a variety of human tumors and precancerous conditions including basal and squamous cells, skin cancers, breast cancer, metastatic to skin, brain tumors, head and neck, stomach, and female genital tract malignancy, cancers and precancerous conditions of the esophagus such as Barrett's esophagus. A review of the history and progress of photoactivated therapy is provided by Marcus, S. Photodynamic Therapy of Human Cancer: Clinical Status, Potential, and Needs. In Gomer, C. J. (ed.); "Future Directions and Applications in Photodynamic Therapy." Bellingham, W. A. SPIE Optical Engineering Press (1990) pp. 5–56 and specific applications of PDT are provided by Overholt et al., *Sem. Surg. Oncol.* 11:1–5 (1995).

One area of focus in the development of phototherapeutic methods and apparatus is the development of targeted light sources that provide uniform illumination to a given treatment area and their use in columnar environments.

Allardice et al. *Gastrointestinal Endoscopy* 35:548–551 (1989) and Rowland et al. PCT application WO 90/00914, disclose one type of light delivery systems designed for use with PDT. The disclosed system involves a flexible tube comprising a dilator and a transparent treatment window. A fiber optic element that is connected to a laser and ends in a diffusing tip is used in combination with the dilator to deliver light to a tissue source. Allardice et al. suggests using a 3 cm long, 1 cm in diameter treatment window for treating a 4 cm long region.

Nseyo et al. *Urology* 36:398–402 (1990) and Lundahl, U.S. Pat. Nos. 4,998,930 and 5,125,925, disclose a spherical balloon catheter device with a radius of 3.7 cm for providing uniform irradiation to the inner walls of hollow organs, such as the bladder.

Panjehpour et al. *Lasers and Surgery in Medicine* 12:631–638 (1992) discloses the use of a centering balloon catheter to improve esophageal photodynamic therapy. Panjehpour discloses a cylindrical balloon catheter, having a cylindrical treatment window 3.6 cm long, into which a fiber optic probe ending in a light diffuser is inserted. The cylindrical balloon was used to deliver three treatments to the esophagus of a dog in a typical study. To treat the entire length of the column requiring treatment, the balloon was advanced into the column while multiple light doses were administered.

Overholt et al. *Lasers and Surgery in Medicine* 14:27–33 (1994) discloses modified forms of the balloon catheter device described by Panjehpour. The cylindrical balloon catheter was modified by coating both ends of the balloon with a black opaque coating to define a 360 degree treatment window of 2.0 to 2.6 cm in length.

Overholt et al. *Gastrointestinal Endoscopy* 42:64–70 (1995) discloses the use of Overholt (1994) balloon catheters for treating Barrett's esophagus. Overholt used treatment windows of 2 to 3 cm in length. Overholt used treatment windows of 2 cm to treat 4 to 7 cm area using multiple light doses while advancing the catheter into the esophagus during a typical treatment regime.

Overholt et al. *Seminars in Surgical Onc.* 11:1–5 (1995) discloses the clinical results of treating 12 patients with Barrett's esophagus using an Overholt (1994) balloon catheter. 2 to 3 cm in length treatment windows were used. Overholt suggests using a balloon catheter with a 2–3 cm treatment window and restricting the treatment length to 5 to 7 cm in a single treatment, even for patients requiring 6 to 10 cm in treatment.

Rowland et al. PCT application WO 90/00420, discloses a light-delivery system for irradiating a surface. The device comprises a hemispherical shell whose inside is entirely coated with a diffuse reflector and a light source that is mounted within the shell. The light source may contain a diffusing source at the tip allowing diffusion of light within the reflective shell.

Spears, U.S. Pat. No. 5,344,419, discloses apparatuses and methods for making laser-balloon catheters. Spears utilizes a process that etches an end of a fiber optic cable to provide a diffusion tip on the optical cable. The optical cable containing the etched tip is secured within a central channel of a balloon catheter using a coating of adhesive containing microballoons. The position of the tip within the central channel and the microballoons contained in the adhesive provide increased efficiency in diffusing the laser radiation in a cylindrical pattern, providing a more uniform illumination at the target site.

Beyer, et al. U.S. Pat. No. 5,354,293 discloses a spherical balloon catheter apparatus for delivering light for use in PDT. The balloon catheter device disclosed employs a conical tipped fiber optic cable to provide means of deflecting a light beam radially outward through a transparent portion of an inflated catheter of 2 cm in diameter.

In summary, there have been numerous devices that have been developed for use in PDT that employ a balloon catheter to support a light source in an ideal central point within a target area that is to be illuminated (Spears, Overholt, Beyer, Lundahl and Allardice) The main benefits of using a centering type balloon are that 1) the clinician does not have to hold the fiber optic in the central location, this is done automatically by the balloon catheter, 2) the light dose is more uniform across the entire treatment area than would be the case of light delivered by a fiber optic that is held central to the treatment volume without the aid of a balloon (while this is true with existing designs of balloon catheters, it is herein demonstrated that the uniformity can be significantly improved), 3) the treatment field is kept clean of contaminants e.g. blood, urine that might absorb the light and so effect the final PDT result, and 4) the overall treatment procedure can be considerably shortened as it is simpler setting up the fiber optic and getting the light dose correct.

Although teaching the use of balloon catheters to provide light to columnar environments, each of the above references that discloses such uses and devices suggest using irradiation segments of 3 cm or less when treating columnar environments such as the esophagus, even when the required treatment length may be longer than 7 cm. The various authors suggest using multiple light doses, each time advancing the light element farther into the columnar environment. The various authors further suggest that treatment lengths be limited to 5 to 7 cm for a particular treatment session.

SUMMARY OF THE INVENTION

The present invention is based on the unexpected observation that the incidence of strictures that form in biological columns during phototherapy can be decreased by employing an extended irradiation segment or window. Based on this observation, the present invention provides improved methods for delivering light to the surface of a biological column wherein the improvement comprises the use of an extended irradiation segment or window. The improved methods of the present invention permits the treatment length to be increased without increasing the incidence of stricture formation.

BRIEF DESCRIPTION OF THE DRAWINGS

FIG. 1 provides a diagrammatic representation of a balloon catheter that has an extended irradiation window.

DETAILED DESCRIPTION OF THE PREFERRED EMBODIMENTS

It has been the exclusive practice in methods that require light or irradiated energy to be delivered to a biological column, such as in treating Barrett's esophagus using PDT, to employ an effective irradiation segment along the length of the column that is approximately equal to or less than the diameter of the expanded column, for example in treating the esophagus, the recommended irradiation segment length using a 1.5 cm to 3.5 cm diameter inflated balloon catheter is 1–3 cm.

The "irradiation segment" is defined as the region receiving irradiation in a single dose without advancing the device further into the biological column. The length of the irradiation segment is determined by the means used to deliver the light, for example, by using a fiber optic diffuser with or without other means for controlling the portion of the column that receives the emitted light, such as a balloon catheter containing an irradiation window or other light-directing means.

In most of conditions that require the irradiation of a biological column, the length that requires treatment is typically 2 to 7 times longer than the irradiation segment. To provide effective treatment, the device used to irradiate the column is advanced down the biological column and multiple light doses are administered to provide an effective dose of irradiation over the length of the biological column requiring treatment.

In most applications of columnar irradiation, there has been found a high incidence in the formation of undesired strictures in the biological column following irradiation. A stricture is an abnormal narrowing of the biological column, typically caused by inflammation or scar tissue. This side-effect of treatment is problematic, especially in the case of the esophagus where subsequent dilation using a non-illuminating catheter may be required in order to allow passage of food or liquids.

The exact mechanism of stricture formation following irradiation therapy remains unknown. The only suggestion for eliminating stricture formation thus far advanced is to decrease the length of the column irradiated during a therapeutic session Overholt et al. *Seminars in Surgical Onc.* 11:1–5 (1995). The disadvantage of using shorter treatments lengths is that a patient will often require more than one session of irradiation therapy to irradiate the entire length of the column that requires treatment.

The present invention provides improved methods for delivering irradiation to a biological column that yields a decrease in the incidence of stricture formation in the biological column when compared to the incidence of stricture formation found with presently known methods. Specifically, the incidence of stricture formation within a biological column following irradiation therapy can be reduced by employing an extended irradiation segment when irradiating the biological column.

As used herein, a "biological column" is defined as a generally tubular tissue, such as esophagus, intestine, blood vessel, bronchial tube, and the like, that may be affected by conditions that require the administration of light. A skilled artisan can readily use the present methods for obtaining reduced incidence of stricture formation with any biological column where stricture formation following light administration is a problem.

As used herein, the "irradiation segment" refers to the portion of the biological column that receives an effective amount of radiation when light is administered in a single doses without advancing the irradiation device in the biological column. The length of the irradiation segment is dependent on the device used to deliver the irradiation.

As used herein, an irradiation segment is said to be "an extended irradiation segment" when the segment is more than about 25% longer than lengths previously suggested for use in treating the particular biological column or condition, more preferably from about 50% to about 100% longer. For example, the previous recommended irradiation segment length used for treating Barrett's esophagus with PDT using an inflatable cylindrical balloon catheter is about 1–2 cm, with a maximum recommended length of about 3 cm. In the present method, the recommended extended irradiation length will be about 4 cm, or longer, and preferably about 7 cm, or longer.

The method used to obtain an extended irradiation segment will depend on the device used to deliver the irradiation and is described in more detail below for the specific use of a balloon catheter. However, in general, it is well within the skill of the art to construct irradiation devices for use in columnar environments that provide irradiation to an extended irradiation segment.

As used herein, irradiation, light or light irradiation, refers to light of wavelengths from about 300 nm to about 1200 nm. This includes UV, visible and infrared light. The choice of wavelength will be based on the intended use, namely being selected to match the activation wavelength of the photoactivated drug or the wavelength used for irradiation when a photoactivated compound is not employed. Examples of photoactivated compounds include, but are not limited to ALA, SnET2, phthalocyanines, BPD, PHOTOFRIN, MACE, psoralen, and derivatives thereof.

As used herein, an "effective amount" of irradiation is defined as the amount of radiation that will be sufficient for the particular therapeutic method. For example, with PDT, an effective amount of irradiation is the energy sufficient to excite the photoactive agent present in the tissue of the column.

In the preferred embodiment, a cylindrical balloon catheter is employed to deliver light to the extended irradiation segment of the biological column, for example, by using a balloon catheter essentially as described by Panjehpour et al. *Lasers and Surgery in Medicine* 12:631–638 (1992), Overholt et al. *Lasers and Surgery in Medicine* 14:27–33 (1994), Overholt et al. *Gastrointestinal Endoscopy* 42:64–70 (1995), and U.S. Ser. No. 08/649,439, entitled "Improved balloon catheter device by Bower, et al.). Balloon catheters comprise an outer inflatable balloon, preferably made up of a nondistendable material and an internal element that provides diffuse light within the lumen of the balloon, such as those described in U.S. Pat. Nos. 5,431,647, 5,269,777, 4,660,925, 5,074,632, 5,303,324 and SBIR application grant 2R44CA60225/02.

Cylindrical shaped balloon catheters typically contain an irradiation window in the balloon catheter that is defined by an absorptive black or reflective/scattering covering on the ends of the balloon, FIG. 1. The irradiation segment provided with a balloon catheter of this configuration is the same length as the irradiation window. Accordingly, to use a balloon catheter to supply light to an extended irradiation segment, an extended irradiation window is used. A more detailed description of a balloon catheter having an extended treatment window is provided below.

When using a balloon catheter device with the methods of the present invention, the size and shape of the balloon and the length of the irradiation window will depend on the intended use. The diameter of the balloon is chosen so as to flatten the folds in the biological column when inflated. The shape is chosen based on the nature of the columnar environment. Typically a cylindrical balloon from about 10 mm to 35 mm in diameter is employed to flatten the folds in the esophagus.

The size of the irradiation window will be chosen to provide an extended irradiation segment when used in a particular biological column for a particular therapeutic method. When a cylindrical balloon catheter is used to irradiate the esophagus using the methods of the present invention, the irradiation window will be from about 40 mm to about 200 mm in length when the balloon is inflated. More preferably the irradiation window will be about 70 mm or longer.

By employing an extended irradiation segment, for example by using an extended irradiation window, the length of the treatment segment can be increased. As used herein, a "treatment segment" refers to the entire length of the biological column that is treated in a single phototherapeutic session. For the treatment of Barrett's esophagus using PDT, the previously recommended treatment length was 4–7 cm when using a 2–3 cm irradiation segment/window. Using an extended irradiation window or segment, it is now possible to have treatment lengths greater than 7 cm, and in some cases, greater than 10 cm in length without an increased incidence in stricture formation.

In one application of using an extended irradiation segment, the irradiation window will be of sufficient length to provide an irradiation segment that is approximately the same length as the region of the column requiring irradiation. In such an application, a single dose of irradiation can be used to provide an effective amount of irradiation to the entire length of the column requiring treatment without an increase in the formation of strictures. Irradiation segments lengths of about 60 mm or greater can be used in the treatment of Barret's esophagus using balloon catheters with treatment windows of about 60 mm to about 100 mm in length.

When used in conjunction with PDT, particularly in the treatment of Barret's esophagus, the improved methods of the present invention can employ any of the art known photosensitizers that are used in photodynamic therapy. Typical among these are porphyrin-derived compounds, chlorins and florins, psoralens, and precursors of the porphyrins. Significant preferred photosensitizers include tin etioporphyrin, Photofrin porfimer sodium, BPD-MA, zinc phthalocyanine, and the precursor alpha levulinic acid (ACA). The protocols and formulations for administering these photoactive agents depend on the type of condition being treated and are generally understood in the art.

The present invention further provides an improved apparatus for delivering light to a biological column, said improvement comprising means for irradiating an extended irradiation segment.

In the preferred embodiment, the means for providing irradiation is a balloon catheter and the improvement comprises an extended irradiation window. In this embodiment, the apparatus comprises a central channel into which a fiber optic probe can be inserted and an outer sleeve having a proximal end and a distal end and containing an inflatable balloon proximal to the distal end.

The balloon portion of the apparatus of the present invention can be manufactured to be any of a variety of shapes when inflated. Such shapes include, but are not limited to, spherical and cylindrical shapes with tapering ends. The preferred shape will depend on the shape and nature of the area of treatment. For example, when treating the esophageal tract, e.g., when treating Barrett's esophagus, a cylindrical shape with tapering ends is preferred.

The size and shape of the balloon and treatment will depend on the intended use. For example, when the device of the present invention is used to treat Barrett's esophagus, the preferred shape is cylindrical and will be from about 10 mm to about 200 mm in length and from about 10 mm to 35 mm in diameter when inflated. The diameter being selected to flatten the folds in the esophagus.

Any semi-resilient material that can form a balloon that can be inflated using either air or fluid can be used in making the balloon component of the present apparatus. The material can be either transparent or translucent. The preferred material will be transparent and non-distendable. The preferred material is a polyurethane membrane of a thickness of about 0.11 mm. However, any material that is used in the construction of other art known inflatable balloon catheters can readily be used in the devices of the present invention.

The balloon used in this embodiment of the apparatus of the present invention contains a material at the ends of the balloon that is either absorptive or that reflects and preferably also scatters light into the lumen and treatment window of the balloon. The material is contained on the ends of the balloon and the area that is not coated with the material defines an irradiation window.

As provided above, the irradiation window is chosen so as to be an extended irradiation window. Specifically, the window size is chosen so as to provide irradiation of an extended irradiation segment when used in an columnar environment. For use in the esophagus, for example in treating Barret's esophagus using PDT, the preferred window size is about 4 cm in length or longer, preferably from about 7 cm to about 20 cm in length.

As used herein, a material is said to be absorptive or reflective if the material prevents from about 20 to 100% of light striking the surface from being transmitted through the material. As used herein, a material is said to be reflective when the material prevents the transmission of light through the material by deflecting the light striking the material. The preferred reflective material will also be able to scatter the deflected light, providing a diffuse reflection of the light hitting the material. The function of the absorptive or reflective material in this configuration is to define a treatment window, to prevent light from exposing non-target areas outside the treatment window, and to provide a greater uniformity in the transmitted light.

FIG. 1 provides a diagrammatic representation of a balloon catheter that contains a coating at both ends (panel a), or a coating at both ends and a coating over a portion of the circumference of the treatment window of the balloon (panel b).

Any coating material that is either absorptive or reflective (and can preferably also scatter the reflected light), can be used as the coating for the balloon component of this embodiment of the apparatus of the present invention. Examples of coating material include, but are not limited to, black colored polymeric material, titanium dioxide, aluminum, gold, silver, and dielectric films. The choice of the material used will depend, in a large part, on the material used in the balloon, the method used to manufacture the balloon and the wavelength of light used in the phototherapy. A skilled artisan can readily adapt known reflective materials for incorporation into the balloon component of the apparatus of the present invention.

The coating can be incorporated in the balloon component of the apparatus of the present invention in a variety of ways. For example, the coating can be applied to the surface of the balloon after the balloon is formed, for example by using a dipping process. Alternatively, the coating can be directly incorporated into the material used to form the balloon during the manufacturing of the balloon. The method used to incorporate the coating into the balloon will be based primarily on the coating material used, the material the balloon is made of, and the method used to manufacture the balloon component. A skilled artisan can readily employ art-known procedures for incorporating a coating material within or onto a surface of a balloon.

The balloon component may further contain optical sensors. Optical sensors that are integral to the balloon component can be used to measure the intensity of illumination when the catheter is used therapeutically. Optical sensors, such as a fiber optic probe or a photodiode as part of a balloon catheter, have been described in U.S. Pat. No. 5,125,925.

The apparatus of the present invention may further comprise a fiber optic cable, a fiber optic bundle or liquid light guide, for convenience, hereinafter referred collectively as a fiber optic cable. The fiber optic cable will contain one end that is readily attachable to a laser or non-laser light source and a second end onto which a diffuser is attached.

The light carrying section of the fiber optic cable, hereinafter the fiber optic core, can be of any diameter so long as the fiber optic cable can be inserted into the central channel of the balloon catheter. The preferred fiber optic core will be from about 50 to about 1000 microns in diameter, preferably about 400 microns. The choice of the core diameter will depend on the brightness of the light source and the optical power output required from the fiber optic diffuser tip.

As stated above, the fiber optic cable will terminate in a diffusion tip or diffuser. As used herein, a diffuser or diffusion tip, is defined as an element that can be attached to the end of a fiber optic cable, or a structure that can be formed at the end of the fiber optic cable, that provides a means for diffusing (scattering) the light being transmitted through the fiber optic cable so that it radiates outward from the fiber. Fiber optic diffusers are readily available and can be created by a variety of methods including, but not limited to, surrounding a central core with a scattering media or a scattering film, tapering the tip of the fiber optic cable to form a conical tip, or by inserting a tapered fiber optic tip into a cylindrical body containing optical scattering media. A variety of diffusion tips for using in PDT apparatus are described in U.S. Pat. Nos. 5,431,647, 5,269,777, 4,660,925, 5,074,632, and 5,303,324. The preferred diffusing tip for the fiber optic cable contained in the apparatus of the present invention is the cylindrical diffusion tip described in SBIR application grant 2R44CA60225/02 and are available from Laserscope (CA).

The length of the diffusion tip can be varied relative to the size of the treatment window defined by the reflective material at the ends of the balloon component. It has been found that the intensity and uniformity of light being transmitted through the treatment window can be optimized by selecting a diffusion tip that is longer than the treatment window. Additionally, the longer diffusion tip eliminates the need for precise positioning of the fiber optic in the center of the treatment window In the Examples that follow, it was found that a diffusion tip that is longer than the treatment window provided an increase in the uniformity of light being transmitted through the treatment window. Preferably, the diffusion tip will extend from about 0.3 cm to about 5 cm on either side of the treatment window.

Recent developments in producing small efficient light emitting diodes (LEDs) permits the use of a probe having multiple LEDs mounted on an end to form a distributed array. Such a probe can replace the fiber optic cable and diffuser by being inserted, LED end first, into the central channel. The LEDs emit a diverging beam of light without the need for a diffuser, although a diffuser can be incorporated into such a probe to increase diffusion. In such a configuration, the LEDs cover the probe to a length equivalent to the diffuser tip and is equivalent to, and referred to as the fiber optic cable or probe.

In an alternative configuration, the balloon component can be provided without the central channel. In such a configuration, a fiber optic cable containing the diffusion tip is connected to the distal end of the balloon and is pulled to a central location when the balloon is inflated.

The catheters of the present invention can be used with any wavelength of light for treating any biological column. The choice of the wavelength will be determined by the intended use. In the examples that follows, 633 nm wavelength light, supplied using a helium neon laser, was used.

This is the activation wavelength for a variety of photoactivated compounds used in PDT. The choice of materials used in each of the components of the catheters of the present invention, and in particular the reflective coating and the overall geometry of the finished assembly, can be specifically tailored to provide the desired properties for a given treatment wavelength and indication being treated.

The following examples are intended to illustrate but not to limit the invention. All of the cited references are herein incorporated by reference.

EXAMPLE 1

23 patients were treated for Barrett's esophagus as described in Overholt et al. *Gastrointestinal Endoscopy* 42:64–70 (1995) using a centering balloon catheter with a 5 cm treatment window, singly or in conjugation with a 3 cm balloon or standard diffuser.

Of the 23 patients, 16 received light irradiation using only a centering balloon with a 5 cm irradiation window. The light dosage ranged from 125 J/cm to 200 J/cm.

In the 16 patients recieving light irradiaition using only a 5 cm window, three strictures occurred, 1 being mild, 2 being moderate. This incidence of stricture occurrence is approximately 18%.

Previous reports using 1–2 cm irradiation windows resulted in a 62% incidence of stricture formation (39 patients studied (Overholt et al., *Am. J. Gastro. Ent.* (1996)).

What is claimed is:

1. A method to deliver light at the surface of a biological column during photodynamic therapy (PDT) said method comprising delivering light to an irradiation segment of the biological column with a balloon catheter having a treatment window and a diffuser or light emitting diode that function or cooperate together to provide uniform light in a single effective dose to said irradiation segment wherein said treatment window is at least 4 cm in length and has a distal end and a proximal end and wherein said diffuser is extended beyond the distal and proximal ends of said treatment window.

2. The method of claim 1 wherein said diffuser is extended from about 0.3 cm to about 5.0 cm beyond the distal and proximal ends of said treatment window.

3. The method of claim 2 wherein said diffuser is extended from about 1.0 cm beyond the distal and proximal ends of said treatment window.

4. A balloon catheter comprising a treatment window in said balloon and a diffuser or a light emitting diode that function or cooperate together to provide uniform illumination in a single effective dose at the surface of a biological column during photodynamic therapy (PDT) wherein said treatment window is at least 4 cm in length and has a distal end and a proximal end and wherein said diffuser is extended beyond the distal and proximal ends of said treatment window.

5. The balloon catheter of claim 4 wherein said diffuser is extended from about 0.3 cm to about 5.0 cm beyond the distal and proximal ends of said treatment window.

6. The balloon catheter of claim 5 wherein said diffuser is extended from about 1.0 cm beyond the distal and proximal ends of said treatment window.

7. A method of preventing excess tissue damage in a biological column during photodynamic therapy (PDT) comprising irradiating an irradiation segment of the biological column with a balloon catheter having a treatment window having a distal end and a proximal end for providing irradiation in a single effective dose to said irradiation segment while preventing excess tissue damage, and a diffuser which is extended beyond the distal and proximal ends of said treatment window for dispersing uniform irradiation to said irradiation segment, wherein said treatment window 4 cm or greater in length, and wherein said excess tissue damage is caused by multiple doses of irradiation or non-uniform irradiation exposure.

8. The method of claim 7 wherein said diffuser is extended from about 0.3 cm to about 5.0 cm beyond the distal and proximal ends of said treatment window.

9. The method of claim 8 wherein said diffuser is extended from about 1.0 cm beyond the distal and proximal ends of said treatment window.

10. A balloon catheter for preventing excess tissue damage in a biological column while irradiating an irradiation segment of the biological column during photodynamic therapy (PDT) comprising a treatment window having a distal end and a proximal end for providing irradiation in a single effective dose to said irradiation segment while preventing excess tissue damage, and a diffuser which is extended beyond the distal and proximal ends of said treatment window for dispersing uniform irradiation to said irradiation segment, wherein said treatment window 4 cm or greater in length, and wherein said excess tissue damage is caused by multiple doses of irradiation or non-uniform irradiation exposure.

11. The balloon catheter of claim 10 wherein said diffuser is extended from about 0.3 cm to about 5.0 cm beyond the distal and proximal ends of said treatment window.

12. The balloon catheter of claim 11 wherein said diffuser is extended from about 1.0 cm beyond the distal and proximal ends of said treatment window.

* * * * *

UNITED STATES PATENT AND TRADEMARK OFFICE
CERTIFICATE OF CORRECTION

PATENT NO.   : 6,146,409
DATED        : Nov. 14, 2000
INVENTOR(S)  : Bergein F. Overholt et al It is certified that error appears in the above-identified patent and that said Letters Patent is hereby corrected as shown below:

UNDER THE TITLE:

"THERAPEUTIC METHODS AND DEVICES FOR IRRADIATING COLUMNAR ENVIRONMENTS", should read:--IMPROVED PHOTOTHERAPEUTIC METHODS AND DEVICES FOR IRRADIATING COLUMNAR ENVIRONMENTS--

Signed and Sealed this

Eighth Day of May, 2001

*Attest:*

NICHOLAS P. GODICI

*Attesting Officer*      *Acting Director of the United States Patent and Trademark Office*

UNITED STATES PATENT AND TRADEMARK OFFICE
CERTIFICATE OF CORRECTION

PATENT NO. : 6,146,409
DATED : November 14, 2000
INVENTOR(S) : Overholt et al.

Page 1 of 1

It is certified that error appears in the above-identified patent and that said Letters Patent is hereby corrected as shown below:

Title page,
Item [22], instead of "September 4, 1996," **the filing date should read
-- September 3, 1996. --**

Signed and Sealed this

Twenty-fifth Day of December, 2001

Attest:

Attesting Officer

JAMES E. ROGAN
*Director of the United States Patent and Trademark Office*